United States Patent
Simon et al.

(10) Patent No.: US 10,369,023 B2
(45) Date of Patent: Aug. 6, 2019

(54) IMPEDANCE PARAMETER POWER CONTROL FOR LOWER LIMB ASSISTIVE DEVICE

(71) Applicant: REHABILITATION INSTITUTE OF CHICAGO, Chicago, IL (US)

(72) Inventors: Ann M. Simon, Chicago, IL (US); Nicholas P. Fey, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 14/070,150

(22) Filed: Nov. 1, 2013

(65) Prior Publication Data
US 2015/0127119 A1 May 7, 2015

(51) Int. Cl.
*A61F 2/50* (2006.01)
*A61F 2/60* (2006.01)
*A61F 2/64* (2006.01)
*A61F 2/66* (2006.01)
*A61F 2/68* (2006.01)
(Continued)

(52) U.S. Cl.
CPC .................. *A61F 2/72* (2013.01); *A61F 2/60* (2013.01); *A61F 2/64* (2013.01); *A61F 2/6607* (2013.01); *A61F 2/68* (2013.01); *A61F 2002/503* (2013.01); *A61F 2002/5033* (2013.01); *A61F 2002/607* (2013.01); *A61F 2002/701* (2013.01); *A61F 2002/704* (2013.01); *A61F 2002/7625* (2013.01); *A61F 2002/7635* (2013.01)

(58) Field of Classification Search
CPC .. A61F 2/68; A61F 2/6818; A61F 2/70; A61F 2/701; A61F 2/704; A61F 2/72; B25J 9/0006; B25J 9/1633
See application file for complete search history.

(56) References Cited

U.S. PATENT DOCUMENTS 5,246,465 A 9/1993 Rincoe et al.
7,313,463 B2 12/2007 Herr et al.
(Continued)

OTHER PUBLICATIONS

International Search Report and Written Opinion of the ISA/EP issued in related application PCT/US2014/063469, dated Jan. 30, 2015, 10 pages.
(Continued)

*Primary Examiner* — Christie L Bahena
(74) *Attorney, Agent, or Firm* — Drinker Biddle & Reath LLP

(57) ABSTRACT

Systems and methods are described that relate to the control of a powered lower limb assistive device with one or more joints, where a controller of the assistive device is configured to receive one or more user-generated signals, determine control information using information in the one or more user-generated signals, select one or more joint impedance parameters of the assistive device for adjustment, and, for a mode and state of the assistive device, adjust the selected joint impedance parameters as a function of the control information. Additionally, systems and methods are described that relate to the control of such an assistive device, where a controller of the assistive device is configured to receive one or more user-generated signals containing information about the ankle angle of the assistive device, and adjust the stiffness of the ankle joint of the assistive device as a function of the ankle angle.

22 Claims, 12 Drawing Sheets

(51) Int. Cl.
  A61F 2/70    (2006.01)
  A61F 2/72    (2006.01)
  A61F 2/76    (2006.01)

(56) References Cited

U.S. PATENT DOCUMENTS

| | | | |
|---|---|---|---|
| 7,641,700 | B2 | 1/2010 | Yasui |
| 8,828,093 | B1* | 9/2014 | Kuiken et al. .................. 623/25 |
| 2004/0088057 | A1 | 5/2004 | Bedard |
| 2006/0197485 | A1* | 9/2006 | Kawai .................. B62D 57/032 318/568.12 |
| 2006/0260620 | A1* | 11/2006 | Kazerooni ........... A61B 5/1038 128/845 |
| 2009/0265018 | A1 | 10/2009 | Goldfarb et al. |
| 2010/0179668 | A1 | 7/2010 | Herr et al. |
| 2011/0098828 | A1 | 4/2011 | Balboni et al. |
| 2011/0125290 | A1* | 5/2011 | Langlois .................. A61F 2/60 623/27 |
| 2011/0257764 | A1 | 10/2011 | Herr et al. |
| 2012/0004736 | A1* | 1/2012 | Goldfarb et al. ............... 623/25 |
| 2012/0083901 | A1 | 4/2012 | Langlois et al. |
| 2012/0136459 | A1 | 5/2012 | Herr et al. |
| 2012/0226364 | A1 | 9/2012 | Kampas et al. |
| 2012/0232673 | A1 | 9/2012 | Kampas et al. |
| 2012/0259429 | A1 | 10/2012 | Han et al. |
| 2012/0283844 | A1 | 11/2012 | Langlois |
| 2013/0024006 | A1 | 1/2013 | Balli et al. |
| 2013/0268090 | A1 | 10/2013 | Goldfarb et al. |
| 2013/0274894 | A1 | 10/2013 | Goldfarb et al. |
| 2013/0310949 | A1* | 11/2013 | Goldfarb .................. A61F 2/68 623/27 |

OTHER PUBLICATIONS

Au, S. K., et al., "Biomechanical Design of a Powered Ankle-Foot Prosthesis", Proceedings of the 2007 IEEE 10th International Conference on Rehabilitation Robotics, Jun. 12-15, 2007, pp. 298-303.
Au, S. K., et al., "Powered Ankle-Foot Prosthesis for the Improvement of Amputee Ambulation", Proceedings of the 29th Annual International Conference of the IEEE EMBS, Aug. 23-26, 2007, pp. 3020-3026.
Au, S. K., et al., "Powered Ankle-Foot Prosthesis: The Importance of Series and Parallel Motor Elasticity", IEEE Robotics & Automation Magazine, Sep. 2008, 15(3):52-59.
Au, S. K., et al., "Powered ankle-foot prosthesis to assist level-ground and stair-descent gaits," Neural Netw, May 2008, 21(4):654-666.
Eilenberg, M., et al., "Control of a Powered Ankle-Foot Prosthesis Based on a Neuromuscular Model," IEEE Transactions on Neural Systems and Rehabilitation Engineering, Apr. 2010, 18(2):164-173.
Fey, N., et al., "3D intersegmental knee loading in below-knee amputees across steady-state walking speeds," Clinical Biomechanics, May 2012, 27(4):409-414.
Fite, K., et al., "Design and Control of an Electrically Powered Knee Prosthesis", Proceedings of the 2007 IEEE 10th IEEE International Conference on Rehabilitation Robotics, Jun. 12-15, 2007, pp. 902-905.
Gailey, R., et al., "Review of secondary physical conditions associated with lower-limb amputation and long-term prosthesis use," Journal of Rehabilitation Research & Development, 2008, 45(1):15-29.
Herr, H., et al., "Bionic ankle—foot prosthesis normalizes walking gait for persons with leg amputation," Proc. R. Soc. B., Feb. 2012, 279(1728):457-464.

Highsmith, M.J., et al., "Kinetic Differences Using a Power Knee and C-Leg While Sitting Down and Standing Up: A Case Report," J Prosthet Orthot, 2010, 22(4):237-434.
Lawson, B.E., et al., "Control of Stair Ascent and Descent with a Powered Transfemoral Prosthesis," IEEE Trans Neural Syst Rehabil Eng, May 2013, 21(3):466-473.
Neptune, R. R., et al., "The effect of walking speed on muscle function and mechanical energetics," Gait & Posture, Jul. 2008, 28(1):135-143.
Rouse, E.J., et al., "Estimation of Human Ankle Impedance during Walking Using the Perturberator Robot", 2012 4th IEEE RAS & EMBS International Conference on BioRob, Jun. 24-27, 2012, pp. 373-378.
Shultz, A., et al., "Preliminary Evaluation of a Walking Controller for a Powered Ankle Prosthesis", 2013 IEEE International Conference on Robotics and Automation, May 6-10, 2013, pp. 4838-4843.
Silverman, A.K., et al., "Compensatory mechanisms in below-knee amputee gait in response to increasing steady-state walking speeds," Gait & Posture, Nov. 2008, 28(4):602-609.
Sup, F., et al., "Design and Control of a Powered Knee and Ankle Prosthesis", 2007 IEEE International Conference on Robotics and Automation, Apr. 10-14, 2007, pp. 4134-4139.
Sup, F., et al., "Design and Control of a Powered Transfemoral Prosthesis," The International Journal of Robotics Reseach, Feb. 2008, 27(2):263-273.
Sup, F., et al., "Self-Contained Powered Knee and Ankle Prosthesis: Initial Evaluation on a Transfemoral Amputee", 2009 IEEE 11th International Conference on Rehabilitation Robotics, Jun. 23-26, 2009, pp. 638-644.
Sup, F., et al., "Preliminary Evaluations of a Self-Contained Anthropomorphic Transfemoral Prosthesis," IEEE/ASME Transactions On Mechantronics, Dec. 2009, 14(6):667-676.
Sup, F., et al., "Upslope Walking With a Powered Knee and Ankle Prosthesis: Initial Results With an Amputee Subject," IEEE Transactions on Neural Systems and Rehabilitation Engineering, Feb. 2011, 19(1):71-78.
Vallery, K., et al., "Reference Trajectory Generation for Rehabilitation Robots: Complementary Limb Motion Estimation," IEEE Transactions on Neural Systems and Rehabilitation Engineering, Feb. 2009, 17(1):23-30.
Varol, H.A., et al., "Powered Sit-to-Stand and Assistive Stand-to-Sit Framework for a Powered Transfemoral Prosthesis," IEEE Int Conf Rehabil Robot, 2009, 645-651.
Winter, D., Biomechanics & Motor Control of Human Gait, 1991, 2nd ed, pp. 249-267, University of Waterloo Press.
Wolf, E.J., et al., "Comparison of the Power Knee and C-Leg during step-up and sit-to-stand tasks," Gait & Posture, Jul. 2013, 38(3):397-402.
Yang, S., et al., "Inertial sensors in estimating walking speed and inclination: an evaluation of sensor error models," Medical & Biological Engineering & Computing, Apr. 2012, 50(4):383-393.
Dolan et al., "Dynamic and Loaded Impedance Components in the Maintenance of Human Arm Posture," IEEE Transactions on Systems, Man, and Cybernetics, vol. 23, No. 3, May/Jun. 1993, pp. 698-709.
Hogan, "Impedance Control: An Approach to Manipulation: Part III—Applications," Journal of Dynamic Systems, Measurement, and Control, vol. 107, Mar. 1985, pp. 17-24.
Hogan, "Controlling Impedance at the Man/Machine Interface," Proceedings of the IEEE International Conference on Robotics and Automation, Scottsdale, AZ, 1989, pp. 1626-1631.
Williamson, "Rhythmic Robot Arm Control Using Oscillators," Proceedings of the 1998 IEEE/RSJ Intl. Conference on Intelligent Robots and Systems, Victoria, B.C., Canada, Oct. 1998, pp. 77-83.

* cited by examiner

IMPEDANCE PARAMETER POWER CONTROL FOR LOWER LIMB ASSISTIVE DEVICE

STATEMENT OF GOVERNMENT SUPPORT

This invention was made with government support under grant W81XWH-09-2-0020 awarded by the United States Army. The government has certain rights in the invention.

BACKGROUND

Lower limb assistive devices, such as lower limb prostheses, orthoses, or exoskeletons, may be used by individuals who need the help of such a device. A prosthesis, for instance, may be used by a person who has lost a lower limb by amputation. An orthosis may be used by a person whose lower limb has been weakened by injury or disease, such as a stroke.

A lower limb assistive device may be powered by an external source, such as a battery and electric motor. Powered lower limb assistive devices assist a user's movement. For instance, when a user of a lower limb assistive device is climbing stairs, the device must provide power when the foot of the device is placed on a stair and the user shifts her weight onto the device, so as to propel the user up the stair. As another example, a user who wishes to move from a sitting to a standing position shifts her weight onto her lower limb(s) and lower limb assistive device. The assistive device must provide power to assist the user in transitioning from a sitting posture to a standing posture. Powered lower limb assistive devices known in the art provide users with limited control over the moment when power is applied and the rate at which power is applied. Amputees without adequate powered control of a lower limb assistive device ultimately end up using their good limb, rather than the assistive device, to bear weight in these and other tasks.

SUMMARY

The embodiments herein relate to a system and a method of providing power control to a lower limb assistive device through adjustment of impedance parameters.

DETAILED DESCRIPTION

Systems and methods relating to a lower limb assistive device having a control strategy are described. The control strategy allows a user to control the rate of power generated by the lower limb assistive device during one or more tasks, such as stair ascent, standing up from a seated position, ankle push-off and knee swing initiation during walking, or other tasks that require power from the lower limb assistive device.

In one embodiment, the lower limb assistive device uses an impedance-based approach for generating joint torques, and modulates one or more impedance parameters, when the lower limb assistive device is in a mode and state, in response to a user generated signal. Modulation of one or more impedance parameters in response to a user generated signal allows the user to control both the timing and the rate of power generated by the lower limb assistive device within the mode and state.

Using one of the embodiments allows a user to ambulate or to stand up from a seated position at a pace he or she desires. Use of one of the embodiments allows a user to stop or un-weight his or her assistive device midway through a task without adversely impacting the user's balance.

Use of one of the embodiments increases power to the ankle of the assistive device when the user increases ambulation speed, allowing different users to walk at different speeds as they would with a sound lower limb without requiring clinical configuration of multiple parameters.

A lower limb assistive device may make use of information from sensors, such as mechanical sensors or electrodes, to determine its mode and its state. The "mode" of an assistive device represents a particular type of activity, such as level walking, climbing stairs, descending stairs, ascending ramps, descending ramps, sit-to-stand, stand-to-sit, or running modes in which the user is bearing weight on the lower limb assistive and using it to move from one point to another, such as walking, stair ascent, stair descent, ramp ascent, ramp descent, or running, are known as ambulatory modes. The "state" of an assistive device represents a particular period of operation of the assistive device during a mode, such as early stance, late stance, swing flexion, and swing extension in level walking and ascending ramp modes. A "task" is a motion of a user while the assistive device is in a particular mode and state. A lower limb assistive device may comprise one or more joints, such as an ankle joint or a knee joint. Each joint may be controlled using virtual impedance parameters particular to that joint, including stiffness (known as "k"), damping (known as "b"), and equilibrium angle (known as "θ" or "theta").

Figure 1:
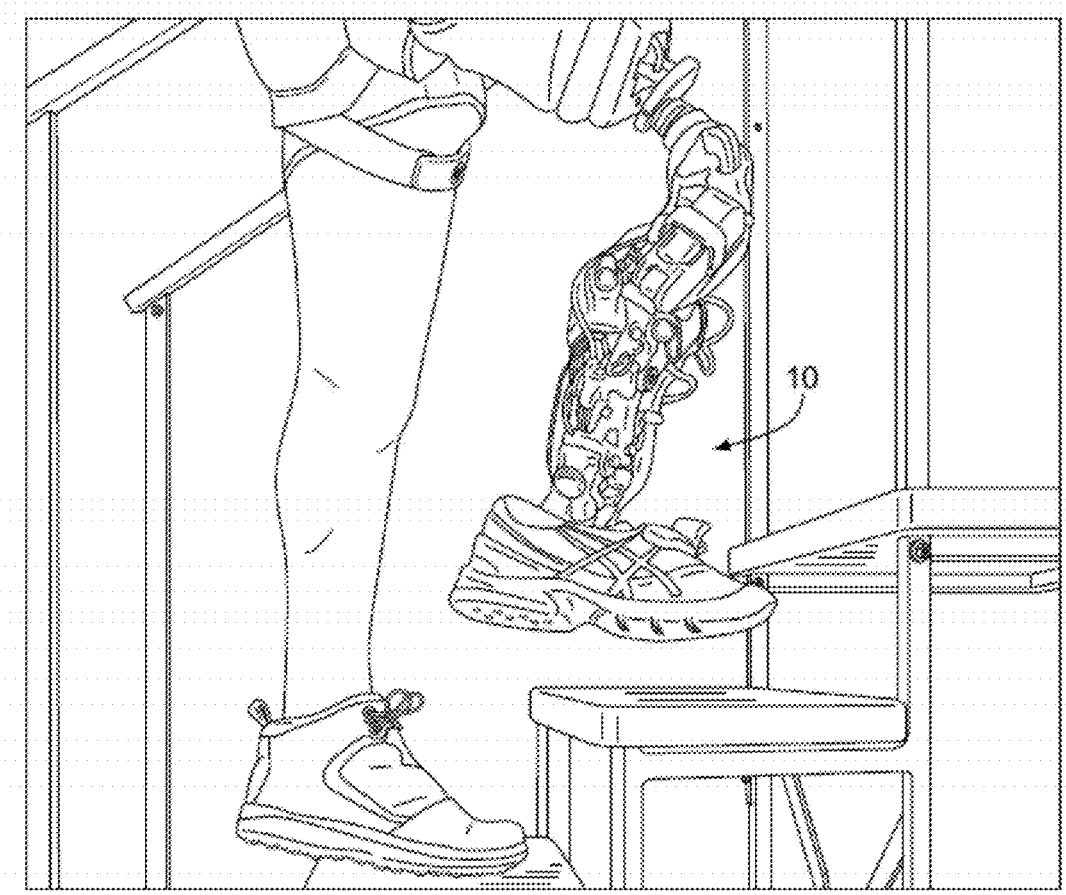
FIG. 1 displays a user wearing prosthesis 10.

A detailed description of embodiments of the invention is provided with reference to the figures. FIG. 1 displays a user wearing prosthesis 10. As discussed in further detail below, during walking, a user of prosthesis 10 will operate prosthesis 10 in four states: early stance, late stance, swing flexion, and swing extension. In the modes of ramp ascent, ramp descent, stair ascent, and stair descent, four similar states may be used, referred to here as stance 1, stance 2, swing 1, and swing 2. In sit-to-stand, two states may be utilized: sit-to-stand, and standing. In stand-to-sit, a single state known here as "stand-to-sit" may be utilized.

Figure 2:
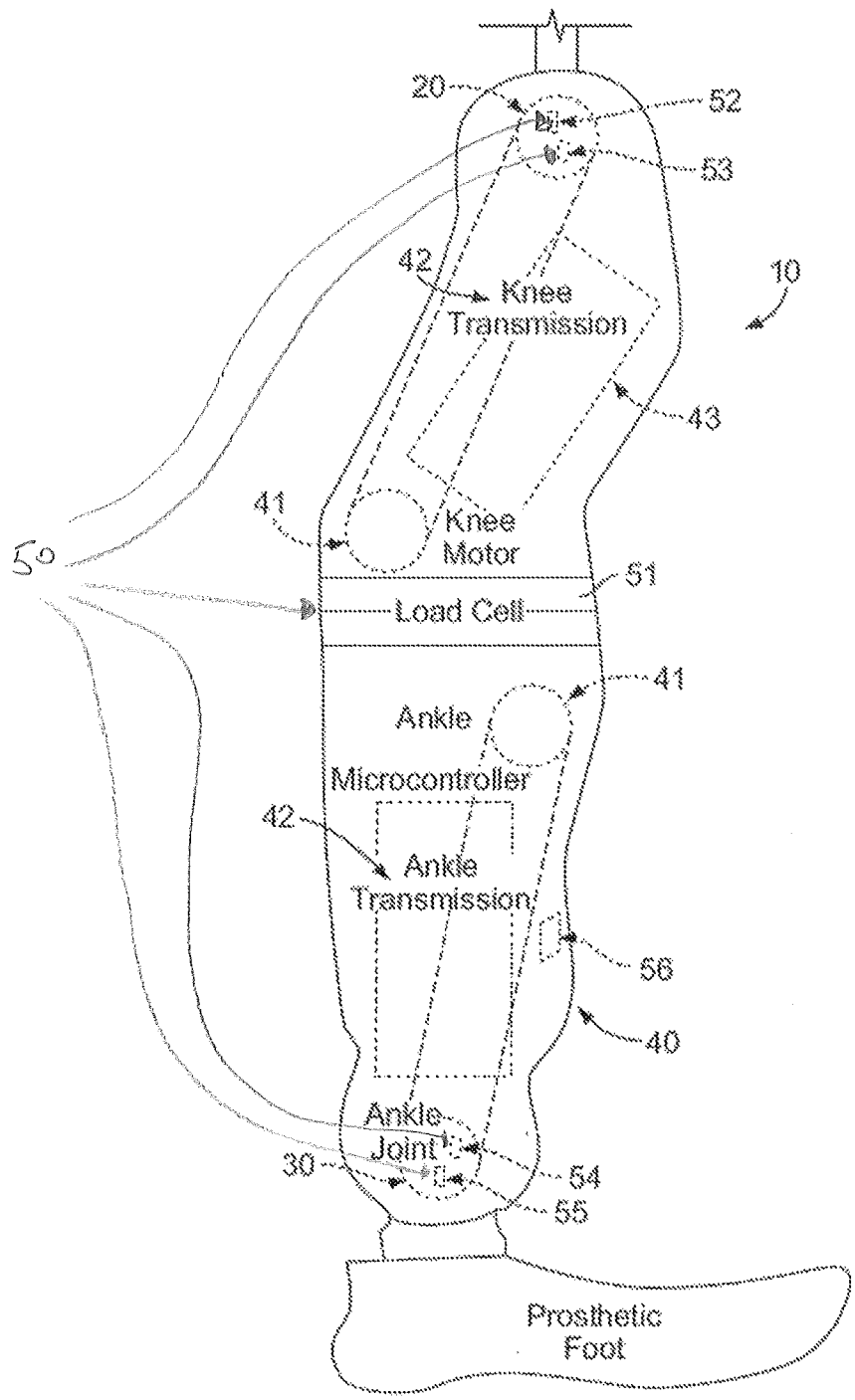
FIG. 2 displays different components of prosthesis 10.

FIG. 2 depicts different components of prosthesis 10. Prosthesis 10 comprises powered knee 20, ankle 30, and shank 40. Knee 20 and ankle 30 are each coupled to one or more motors 41 and one or more transmissions 42 that together are capable of producing physiological levels of torque. Assistive device 10 and its related powered components are powered by battery 43.

Prosthesis 10 further comprises mechanical sensors 50. In one embodiment, mechanical sensors 50 include load cell 51 that measures the load (force) along the long axis of assistive device 10; position sensor 52 and velocity sensor 53 that measure the position and velocity of the knee 20; position sensor 54 and velocity sensor 55 that measure the position and velocity of ankle 30; and a six degree of freedom inertial measurement unit 56 at shank 40, comprising accelerometers and gyroscopes for measuring accelerations and angular velocities. Mechanical sensors 50 may be contained within the assembly of prosthesis 10, attached to prosthesis 10, or attached to the user of prosthesis 10. In other embodiments, knee 20 and ankle 30 could be powered instead with hydraulics, compressed gas, or other mechanisms.

Figure 3:
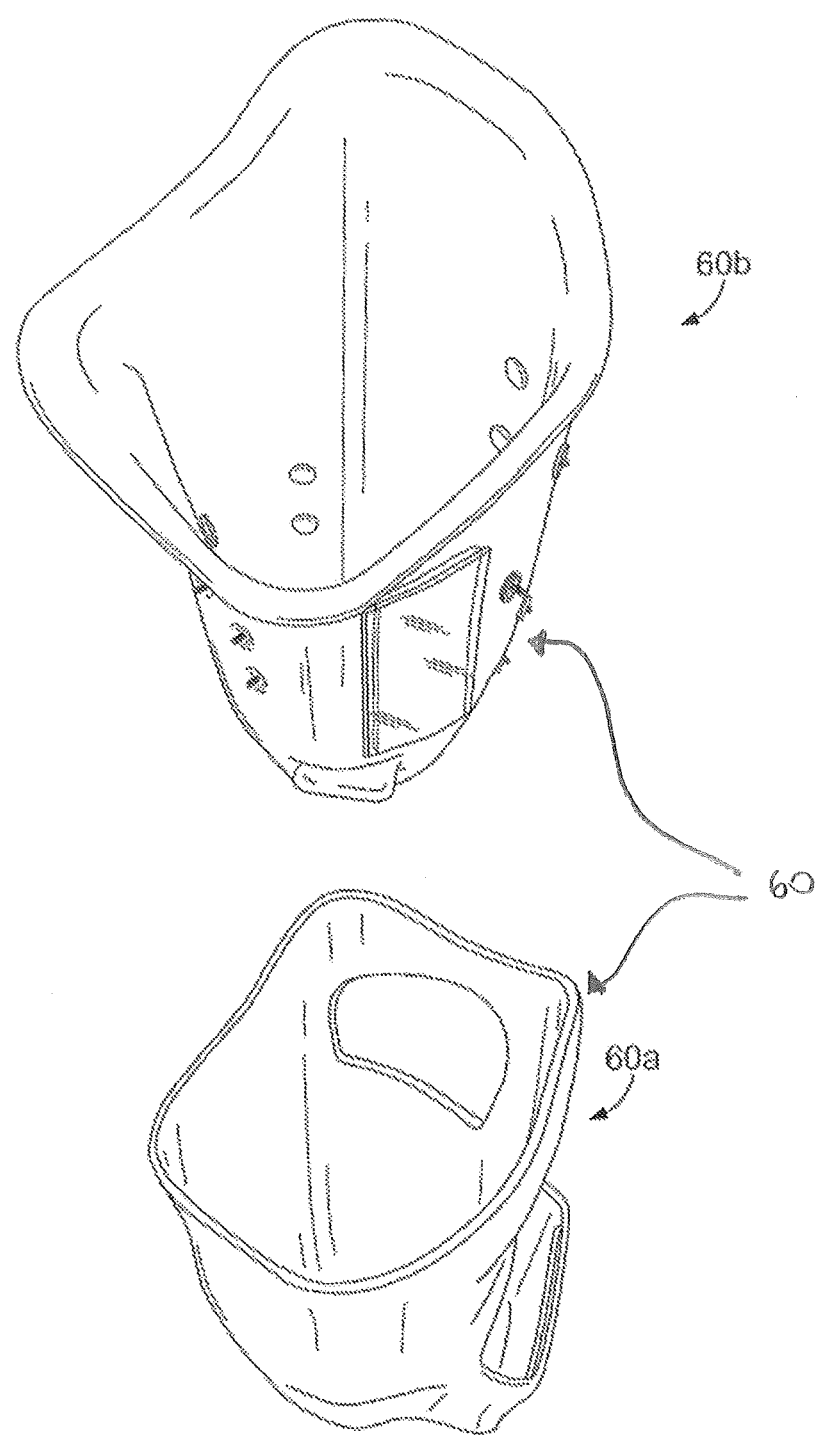
FIG. 3 displays a socket 60.

FIG. 3 displays a socket 60, into which fits the residual limb of a user. Socket 60 comprises lining 60a and exterior shell 60b. Assistive device 10 is coupled to socket 60 by a pyramid style connector or other appropriate connector. Socket 60 is coupled to electrodes 70. In one embodiment, electrodes 70 are embedded in socket 60 and contact the user's skin. As is known in the art, electrodes 70 can measure muscle activity, such as EMG signals from the user's residual limb muscles when the user operates prosthesis 10. In one embodiment, electrodes 70 may be placed on the following muscles of the user: semitendinosus, biceps femoris, tensor fasciae latae, rectus femoris, vastus lateralis, vastus medialis, sartorius, adductor magnus, and gracilis.

Figure 4:
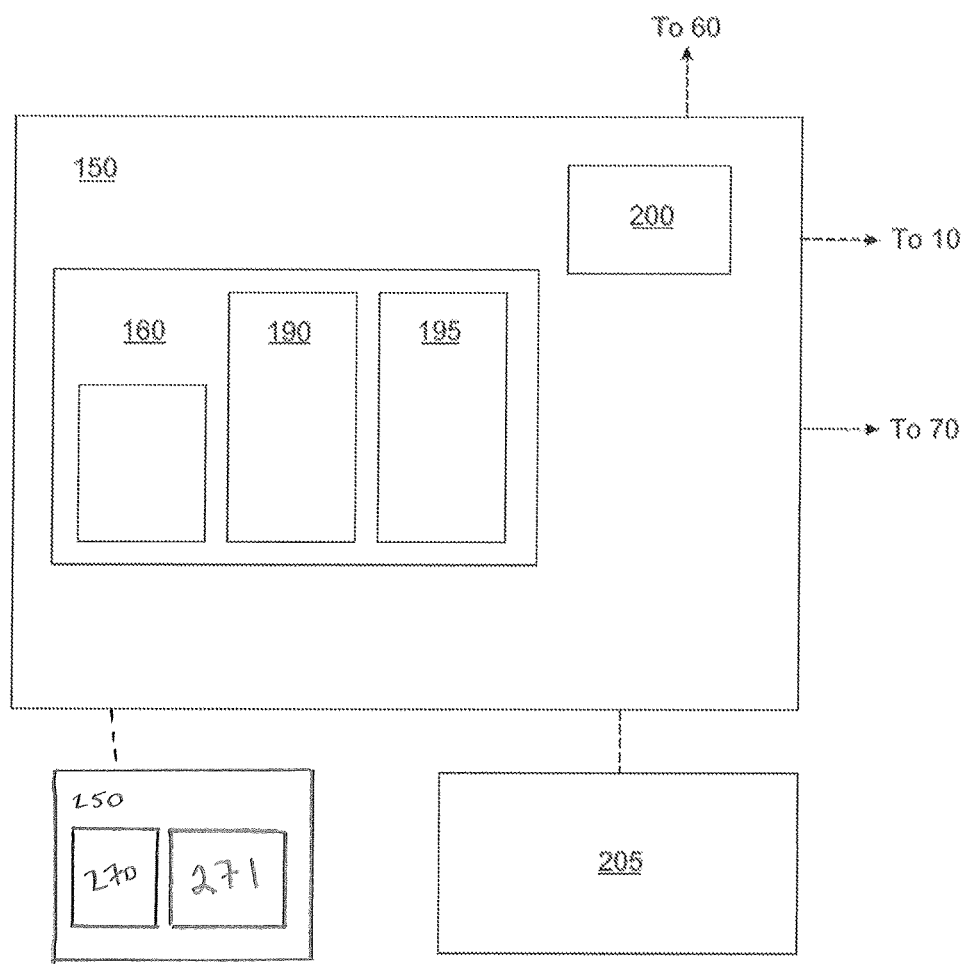
FIG. 4 displays a layout of controller board 150.

FIG. 4 displays a layout of controller board 150. Controller board 150 is one embodiment of a controller used to control prosthesis 10.

In one embodiment, controller board 150 is physically attached to socket 60 and connected to the components of assistive device 10 and to electrodes 70 by communication bus 165. Controller board 150 may comprise an off-the-shelf component, such as the Overo® Air Computer-On-Module (GUM3503A) (GumStix) or a custom built component. Controller board 150 comprises microprocessor controller 160, such as the Texas Instruments OMAP 3503 Applications Processor with processor speed of 600 MHz, or another appropriate microprocessor. Microprocessor controller 160 comprises non-volatile memory 190 and RAM memory 195. As is known in the art, controller board 150 is configured to receive signals from mechanical sensors 50 and electrodes 70. Signals from electrodes 70 are bandpass filtered in hardware between 20 Hz and 420 Hz and digitally sampled at 1000 Hz. Signals from mechanical sensors 50 are sampled at 500 Hz and the signals from load cell 51 are low pass filtered at 20 Hz.

Controller board 150 further comprises transceiver 200 for communication with other components, such as computer unit 250. In one embodiment, transceiver 200 may be a wireless transceiver that is compatible with 802.11, Bluetooth, FM radio, or another wireless standard. Controller board 150 and its components may be powered from main battery 43 or by external power source 205, which provides power conditioning separate from main battery 43 and may comprise a 12V or 20V lithium polymer battery. The details of the components on controller board 150 are exemplary and other components could be used.

Controller board 150 communicates via transceiver 200 with computer unit 250. Computer unit 250 comprises a display, an input device (such as a keyboard, mouse, and/or touchpanel), a wireless module, a hard drive, a processor, an operating system, memory, and other known aspects of a computer system. Embodiments of computer unit 250 include, but are not limited to, a desktop computer system, a laptop computer system, a smartphone system, a tablet computer system, and other similar computer systems known in the art. Computer unit 250 is installed with control software 270 that provides a graphical user interface (GUI) 271. GUI 271 allows a user to communicate with controller board 150 in order to control and receive information from prosthesis 10.

Microprocessor controller 160 is programmed with a control module that contains logic to operate prosthesis 10. In one embodiment, the control module is programmed in Matlab, although other programming languages may be used. Mechanical sensor data from mechanical sensors 50 and load cell 51 coupled to prosthesis 10 are sampled at 500 Hz. Sampling at this or a similarly fast rate allows control module 150 to determine the near instantaneous axial load, knee and ankle joint position, joint velocity, and motor current of prosthesis 10, when prosthesis 10 is on and in operation by a user.

As prosthesis 10 operates, it regularly receives information, including information contained in signals sent from mechanical sensors 50 and electrodes 70, and sets the mode and state of prosthesis 10 in response to at least a portion of the received information. Control board 150 may be used to set the state and mode of prosthesis 10. In one embodiment, prosthesis 10 may be coupled by wired or wireless means known in the art to a computing device optionally having a graphical user interface or another interface (such as an actuator interface) that allows the user to manually set the mode of prosthesis 10. Information from the computing device may be used by control board 150 to set the mode of prosthesis 10. In another embodiment, prosthesis 10 may be coupled by wired or wireless means to a remote control device with buttons or other actuators that allow the user to manually set the mode of prosthesis 10. Information from the remote control device may be used by control board 150 to set the mode of prosthesis 10. In yet another embodiment, control board 150 comprises a classifier, such as a pattern recognition classifier, that sets the mode of prosthesis 10 in response to information such as that contained in one or more signals from mechanical sensors 50 or electrodes 70.

Additionally, as prosthesis 10 operates, control board 150 determines the load on prosthesis 10. In one embodiment, the load may be the axial load on prosthesis 10, determined from information in a signal from load cell 51. Load cell 51 may be positioned in series between the ankle and the knee. In one embodiment, load cell 51 comprises a single axis load cell that measures load on the axis parallel to prosthesis 10. In another embodiment, load cell 51 comprises a multi-axis (such as two-axis or three-axis) load cell that provides information in a signal that control board 150 may use to compute a resultant load on the prosthesis 10. In yet another embodiment, load cell 51 may be used in combination with an inertial measurement unit (IMU) that sends orientation information in a signal that allows control board 150 to determine the vertical load on the prosthesis 10.

Control board 150 additionally determines the state of prosthesis 10 while it operates. In one embodiment, if prosthesis 10 has transitioned to a new mode, control board 150 sets prosthesis 10 to a starting state for that mode. In various embodiments, the selection of a starting state in a new mode could be determined in response to signals from mechanical sensors 50 (such as a signal from load sensor 51 indicating weight on prosthesis 10), a predetermined state machine that indicates the starting state when transitioning to the new mode from the old mode, or another method, known in the art.

If prosthesis 10 has not transitioned to a new mode, it may have transitioned to a new state within the mode. In one embodiment, assistive device 10 has four states each of the following modes: walking, ramp ascent, ramp descent, stair ascent, and stair descent. The states may be referred to generally as stance 1, stance 2, swing 1, and swing 2.

In walking mode, stance 1 is early stance, stance 2 is late stance, swing 1 is swing flexion, and swing 2 is swing extension. Control board 150 causes assistive device 10 to transition from swing 2 to stance 1 upon heel strike. Heel strike may be determined, for instance, when the axial force registered by load sensor 51 is greater than a threshold value. Control board 150 causes assistive device 10 to transition from stance 1 to stance 2 in response to a dorsiflexion threshold crossing, which may be determined by the signal from position sensor 54. Control board 150 causes assistive device 10 to transition from stance 2 to swing 1 upon toe-off. Toe-off may be determined, for instance, when the axial force registered by load sensor 51 is less than a threshold value. Control board 150 causes assistive device 10 to transition from swing 1 to swing 2 upon crossing a knee velocity threshold that may be determined, for instance by the signal from knee velocity sensor 55.

Table 1 sets out the threshold types that trigger a state change within other ambulatory modes:

TABLE 1

|  | Swing 2 to Stance 1 | Stance 1 to Stance 2 | Stance 2 to Swing 1 | Swing 1 to Swing 2 |
| --- | --- | --- | --- | --- |
| Ramp Ascent | Axial load | Dorsiflexion angle | Axial load | Knee velocity |
| Ramp Descent | Axial load | Dorsiflexion angle | Axial load | Knee velocity |
| Stair Ascent | Axial load | Axial load | Axial load | Knee velocity |
| Stair Descent | Axial load | Axial load | Axial load | Knee velocity |

In one embodiment, the dorsiflexion threshold for ramp ascent, level walking, and ramp descent may be set to reflect user preference. For instance, the threshold may be set to 10 degrees for ramp ascent, to 8 degrees for level walking, and to 6 degrees for ramp descent. In other embodiments, control board 150 could transition prosthesis 10 between states in response to a sagittal moment, or could rely on information in signals from other mechanical sensors 50, such as knee torque, to transition between states.

If prosthesis 10 is in sit-to-stand mode, an axial force threshold, reflecting that the user has begun to put weight on prosthesis 10, causes prosthesis 10 to transition to a sit-to-stand state. Prosthesis 10 transitions out of the sit-to-stand state if a lower axial force threshold is triggered (reflecting that the user is no longer putting weight on the prosthesis 10). Prosthesis 10 also transitions out of the sit-to-stand state, and into a standing state, if the angle of knee 30 is straight (reflecting that the user has stood up).

Once prosthesis 10 is set with a mode and state, control board 150 may adjust the impedance parameters for that particular mode and state. In one embodiment, control board 150 may adjust ankle stiffness as a function of ankle angle, for certain modes and states described in more detail below. In other embodiments, control board 150 may additionally, or separately, adjust joint impedance as a function of information in a user-generated signal, for certain modes and states described in more detail below.

Adjusting Ankle Stiffness as a Function of Ankle Angle.

Control board 150 may adjust ankle stiffness as a function of ankle angle. In one embodiment, if prosthesis 10 is in level-ground walking, ramp ascent, or ramp descent mode and in stance 1 or stance 2 states, the control board 150 adjusts ankle stiffness as a function of joint angle. In one embodiment, the control board receives the signal from position sensor 54 and determines the ankle joint angle using information in the signal, as is known in the art. In one embodiment, control board 150 adjusts ankle angular stiffness $k_{ankle}$ as follows in Equation 1:

$$k_{ankle} = W \times (13.6 \times \theta_{ankle} + 1.6) k_{ankle} = W \times (13.6 \times \theta_{ankle} + 1.6)$$

where k represents ankle angular stiffness (Nm/rad), and W represents the user's body mass (kg). Equation 1 is constrained to increase $k_{ankle}$ throughout stance 1 and stance 2 only as the ankle dorsiflexes. As a result, stiffness is relatively low at the beginning of stance 1 and relatively high at the end of stance 2, providing a smoother heel strike, improved stance characteristics, and more comfortable gait for the user.

Adjusting Other Impedance Parameters as a Function of Control Information in a User-Generated Signal.

Control board 150 may adjust other impedance parameters of prosthesis 10 as a function of control information determined using information in one or more user-generated signals. As used here, a user-generated signal is a signal produced or measured by one or more sensors, such as mechanical sensors 50 or electrodes 70, that is generated in response to a movement by the user. For example, load sensor 51 produces a user-generated signal when the user transitions her weight onto prosthesis 10. As another example, an electrode 70 produces a user-generated signal upon detection of a user's muscle activity, such as in the form of an EMG signal. As yet another example, a torque sensor in communication with a joint produces a user-generated signal when the user transitions her weight onto the prosthesis in such a way that causes rotation about the joint.

Figure 5A:
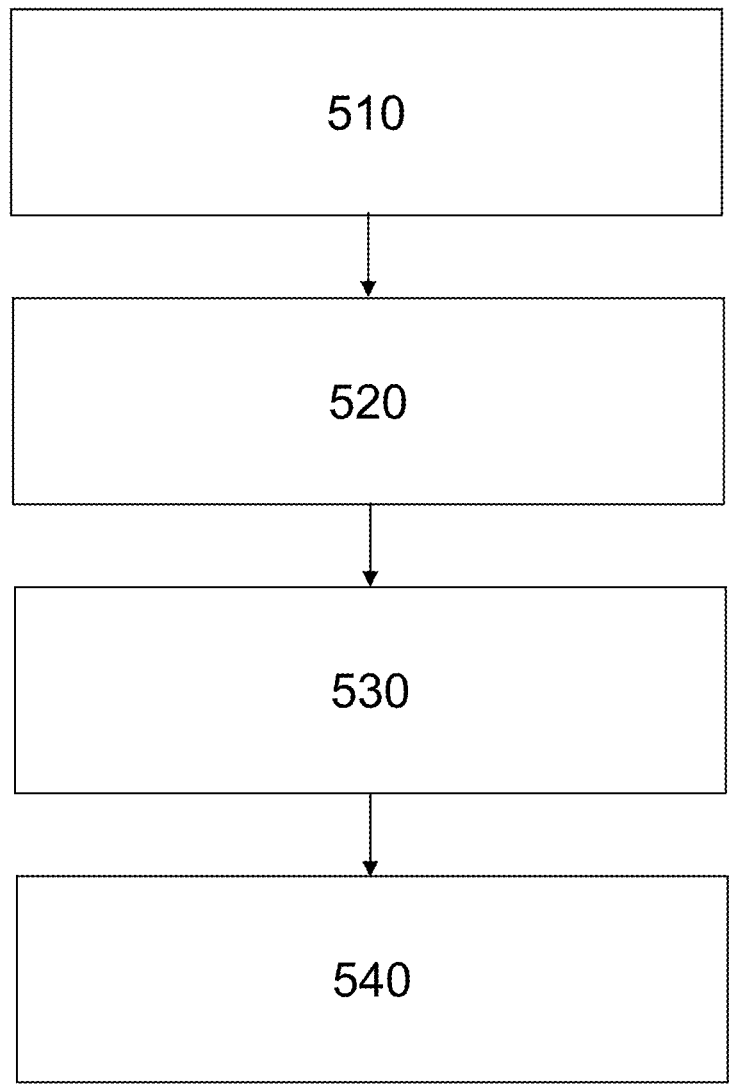
FIG. 5A is a flowchart of one embodiment of operation of control board 150.

FIG. 5A displays a flowchart of one embodiment of the operation of control board 150 for controlling prosthesis 10. In 510, control board 150 receives one or more user-generated signals. In 520, control board 150 determines control information using information in the one or more user-generated signals. In 530, control board 150 selects one or more joint impedance parameters of the assistive device for adjustment. In 540, for the current mode and state of the prosthesis 10, control board 150 adjusts the selected joint impedance parameters as a function of the control information.

In one embodiment, the control information determined by information in a user-generated signal is the axial load being placed on prosthesis 10 while operated by a user. Since axial load on prosthesis 10 can reflect the weight a user places on prosthesis 10, adjusting certain impedance parameters in response to the axial load results in greater user control over the power provided by prosthesis 10.

In one embodiment, control board 150 adjusts certain impedance parameters as a function of axial load. If prosthesis 10 is in walking, ramp ascent, ramp descent modes during stance 2, impedance module 150 adjusts $\theta_{knee}$, $\theta_{d\_ankle}$, and $\theta_{d\_knee}$ in order to reduce knee stiffness, power plantar flexion, and initiate swing as the load on prosthesis 10 decreases. If prosthesis 10 is in stair ascent mode during stance 1 or stance 2, impedance module 150 adjusts $\theta_{d\_ankle}$. As a result, power generation at the knee 20 increases as load on prosthesis 10 increases. If prosthesis 10 is in stair ascent mode during stance 2, control board 150 adjusts $\theta_{d\_ankle}$. As a result, power generation increases at ankle 30 through plantar flexion, as the axial load on prosthesis 10 decreases. If prosthesis 10 is in stair descent mode during stance 1, control board 150 adjusts $\theta_{d\_ankle}$. As a result, power generation increases at ankle 30 through dorsiflexion, as the axial load on prosthesis 10 increases. If prosthesis 10 is in sit-to-stand mode and in the sit-to-stand state, control board 150 adjusts $\theta_{d\_ankle}$ and $\theta_{d\_ankle}$. As a result, power generation increases at knee 20 and ankle 30 as axial load on the prosthesis 10 increases.

In one embodiment, control board 150 adjusts the impedance parameters provided above using Equation 2, as a function of axial load on the prosthesis 10, as follows:

$$p_i = C_i \times \left(\frac{F - F_{Initial}}{F_{Initial} - F_{Final}}\right) \times (p_{i,Initial} - p_{i,Final}) + p_{i,Initial}$$

where i is an index corresponding to the joint (e.g. the knee or the ankle), p represents the impedance parameter to be modulated, and $p_{i,Initial}$ and $p_{i,Final}$ are the desired initial and final values of the parameter within a state. F represents the axial load in the prosthesis as determined by control board 150. $F_{Initial}$ and $F_{Final}$ are the values of F expected at the beginning and end of the state, respectively. C scales the rate at which the impedance parameter changed as a function of axial load. The value of C may be constrained to be greater than or less than 1 and $p_i$ constrained to be between $p_{i,Initial}$ and $p_{i,Final}$. In one embodiment, $C_{ankle}$ may be set to 1.5 and $C_{knee}$ may be set to 1.0. Table 2 provides sample values that may be used by control board 150 to adjust impedance parameters:

TABLE 2

| | $p_{i, Initial}$ | $p_{i, Final}$ | $F_{Initial}$ | $F_{Final}$ |
|---|---|---|---|---|
| Ankle equilibrium angle $\theta_{d\_ankle}$ | Value in stance 1 (0) | Amount of desired plantarflexion (10-15) | Axial load value upon entering stance 2 | Axial load value upon entering swing 1 (0.3) |
| Knee stiffness $k_{knee}$ | Value in stance 1 (2.5-3.0) | Value in swing 2 (0.4) | Axial load value upon entering stance 2 | Axial load value upon entering swing 1 (0.3) |
| Knee equilibrium angle $\theta_{d\_knee}$ | Value in stance 1 (0) | Value in swing 2 (65-75) | Axial load value upon entering stance 2 | Axial load value upon entering swing 1 (0.3) |

The values in Table 2 may be modified by a clinician to improve the experience for a specific user. For example, $p_{i,Final}$ for knee angle may be adjusted for specific users, as the residual limb of each amputee user has a different length, and each user has a different style of ambulation. These factors may require $p_{i,Final}$ for $\theta_{d\_knee}$ to be adjusted, to add more or less swing clearance as desired.

In other embodiments, $p_i$ could be adjusted when prosthesis 10 is within a state and mode using control information determined from other information in one or more user-generated signals. For example, $p_i$ could be adjusted when prosthesis 10 is within a state and mode using control information determined from information in one or more signals from electrodes 70. Control board 150 may adjust $p_i$ as a function of control information determined from information in one or more signals from electrodes 70 in addition to the load on prosthesis 10. In one embodiment, the value of C may be modulated by information in one or more signals from electrodes 70. For example, if prosthesis 10 is in walking, ramp ascent, ramp descent modes during late stance, $C_{knee}$ and $C_{ankle}$ may be increased or decreased by more or less muscle activity recorded from electrodes 70. In another embodiment, control board 150 may adjust $p_i$, for a particular state and mode, as a function of control information determined from information in one or more signals from electrodes 70 rather than as a function of the load on prosthesis 10. In another embodiment, control board 150 may adjust $p_i$, for a particular state and mode, as a function of control information determined from information in one or more signals from mechanical sensors 50. For example, control board may adjust $p_i$ as a function of control information determined using load information from one or more user-generated signals, such as a torque, a moment (e.g., a sagittal plane moment), or another rotational load. If rotational load is used as the control information, control board 150 could determine the rotational load by receiving signals from a load cell known in the art that measures rotational loads.

In addition to adjusting one or more of the specific impedance parameters described above, control board 150 also may adjust remaining impedance parameters, either by keeping them constant, or otherwise adjusting them as known in the art. As is known in the art, adjusting joint impedance parameters of prosthesis 10 causes changes in the torque applied to the joint, which adjusts the amount of power the joint provides to the user.

Figure 5B:
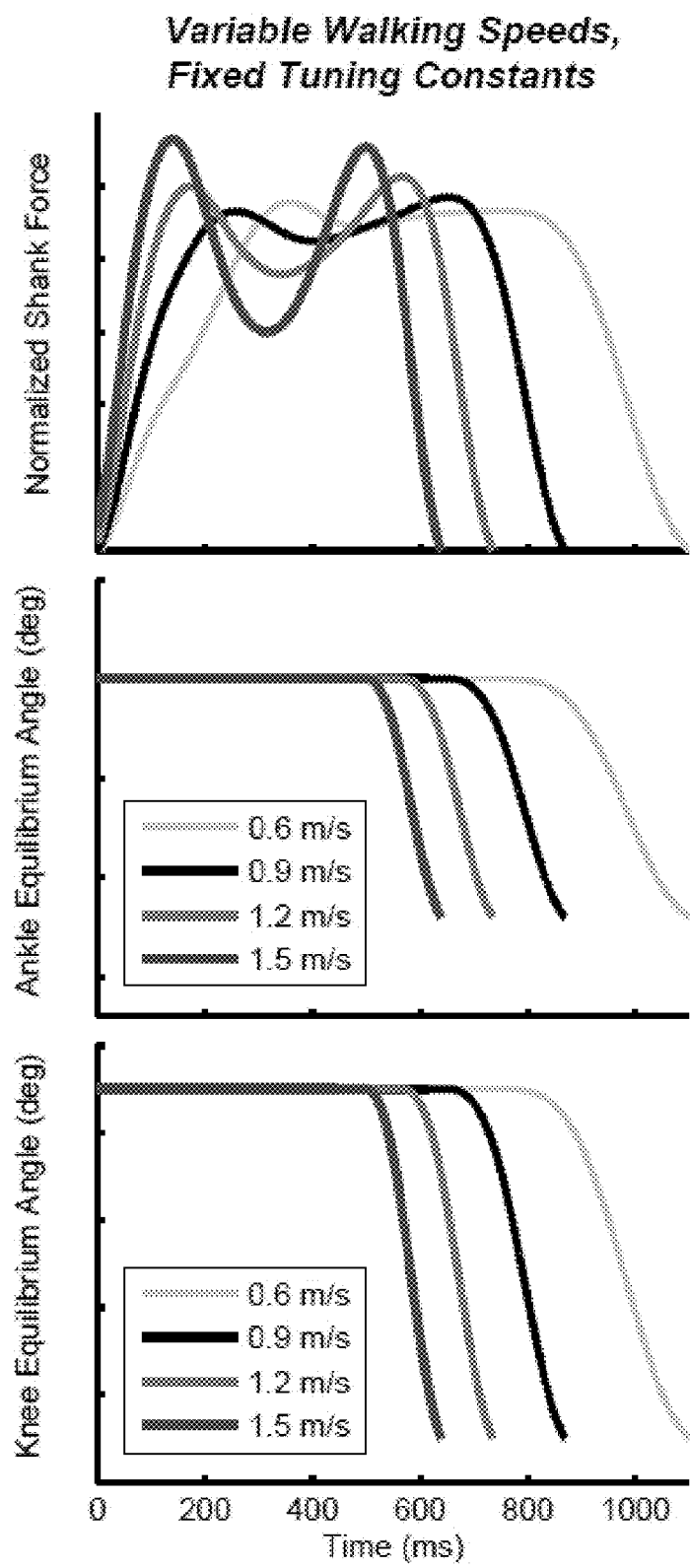
FIG. 5B displays a graph of ankle and knee equilibrium values of prosthesis 10, at different walking speeds, adjusted as a function of load. The ankle and knee equilibrium graphs indicate that the slope of the equilibrium angle for ankle and knee gets steep as the user walks more quickly, and that the ankle and knee angles begin to change immediately as the user begins to unload the prosthesis to take her foot off the ground.

Adjusting the impedance parameters within a particular state and mode of prosthesis 10 results in improved control by a user. In one example, a user may wear prosthesis 10 in place of an amputated right leg. The user may wish to alter her speed of gait in level walking mode. As shown in FIG. 5B, when prosthesis 10 enters the stance 2 state, control board 150 adjusts the equilibrium angles of the knee ($\theta_{d\_knee}$) and ankle ($\theta_{d\_ankle}$) to begin to flex the knee and plantarflex the ankle as a function of decreasing axial load. The duration of stance changes as walking speed changes. Likewise, adjusting the equilibrium angle as a function of decreasing force enables the stance-to-swing transition to be well-timed and performed smoothly. Furthermore, the rate at which the equilibrium angles change is proportional to the rate at which force decreases. In another example, as a user becomes more familiar using prosthesis 10 to climb stairs, she may wish to alter her rate of stair climbing. Upon the user shifting weight to the prosthesis 10 within the specific mode and state, the control board 150 adjusts impedance parameter $\theta_{d\_knee}$ to provide knee power to assist the user in climbing the stair. If the user has just begun to learn how to increase her weight on the prosthesis 10 as she climbs stairs, the knee equilibrium angle will change more slowly because the rate of force increase will be slower. As a result, the user is allowed to climb the stairs more slowly while prosthesis 10 provides an appropriate amount of power for the speed at which she is climbing. As the user becomes more comfortable using the prosthesis in the stair climbing mode, she can increase the load on prosthesis 10 by distributing more weight on prosthesis 10. The additional weight causes control board 150 to adjust impedance parameter $\theta_{d\_knee}$ (knee equilibrium angle) more quickly. The rates of change of an impedance parameter such as $\theta_{d\_knee}$ are adjusted in response to the user-generated signal, such as the axial load on prosthesis 10, and do not require any manual changes in device configuration by a clinician to alter the device performance within a mode and state.

Another example of use pertains to increasing safety of using powered lower limb assistive devices. A user may be in stair ascent mode, and shift her weight onto prosthesis 10, thus entering prosthesis 10 into stance 1 state. Upon the shifting of her initial weight, control board 150 adjusts impedance parameter $\theta_{d\_knee}$, providing knee power to help the user climb a stair. If halfway through stance, however, the user loses her balance, she will shift her weight off prosthesis 10. Upon shifting weight off of the prosthesis, control board 150 determines that load is no longer increasing, and so stops adjusting impedance parameter $\theta_{d\_knee}$. No additional torque is applied to the knee. As a result, prosthesis 10 is not driven into full knee extension, which allows the user to more safely take weight off the prosthesis and onto her sound limb. This example is applicable also to a user in a sit-to-stand mode and state. As the user begins to generate an increasing load on prosthesis 10 (for instance, when standing up from a sitting position) and then shifts weight off of prosthesis 10, control board 150 ceases to change the equilibrium angles of the knee and ankle. This allows the user to take a break and reattempt the sit-to-stand movement without prosthesis 10 fully extending while the user has not moved to a fully standing position.

Figure 6:
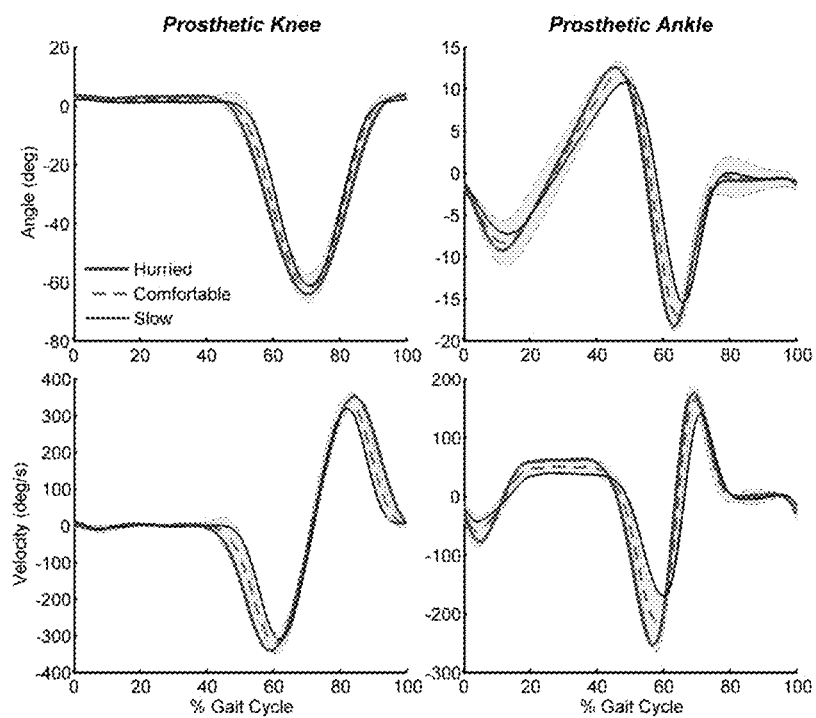
FIG. 6 displays a graph of group-averaged knee and ankle angles and velocities of multiple transfemoral amputees using prosthesis 10 and control board 150 to walk at various level ground walking speeds.
Figure 7:
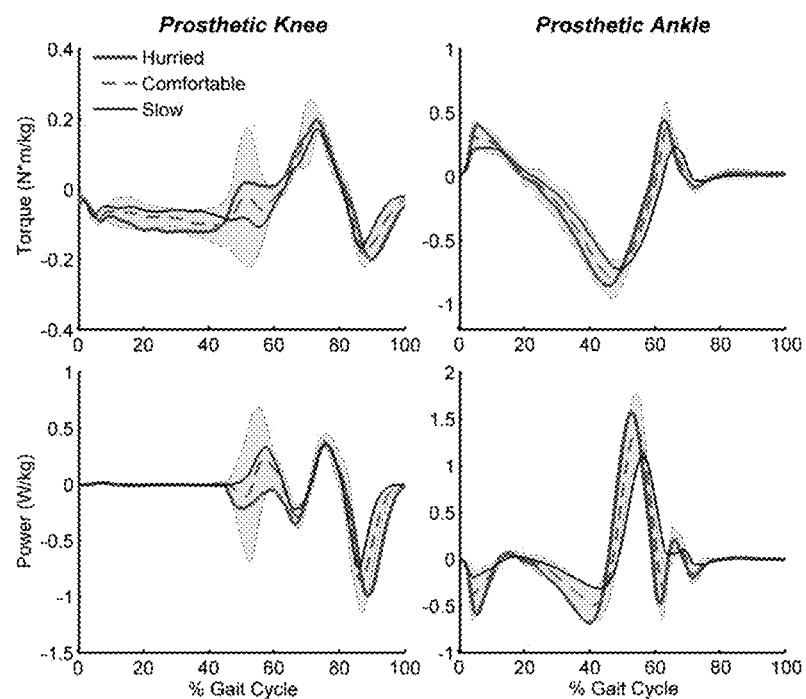
FIG. 7 displays a graph of group-averaged knee and ankle torques and powers of multiple transfemoral amputees using prosthesis 10 and control board 150 to walk at various level ground walking speeds.
Figure 8:
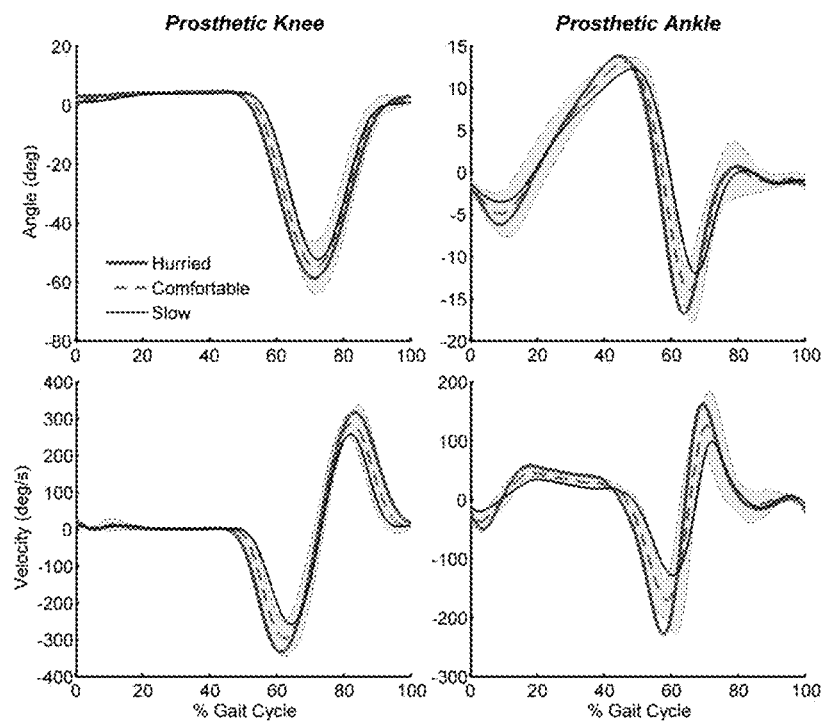
FIG. 8 displays a graph of group-averaged knee and ankle angles and velocities of multiple transfemoral amputees using prosthesis 10 and control board 150 to walk up a ramp (incline) at various speeds.
Figure 9:
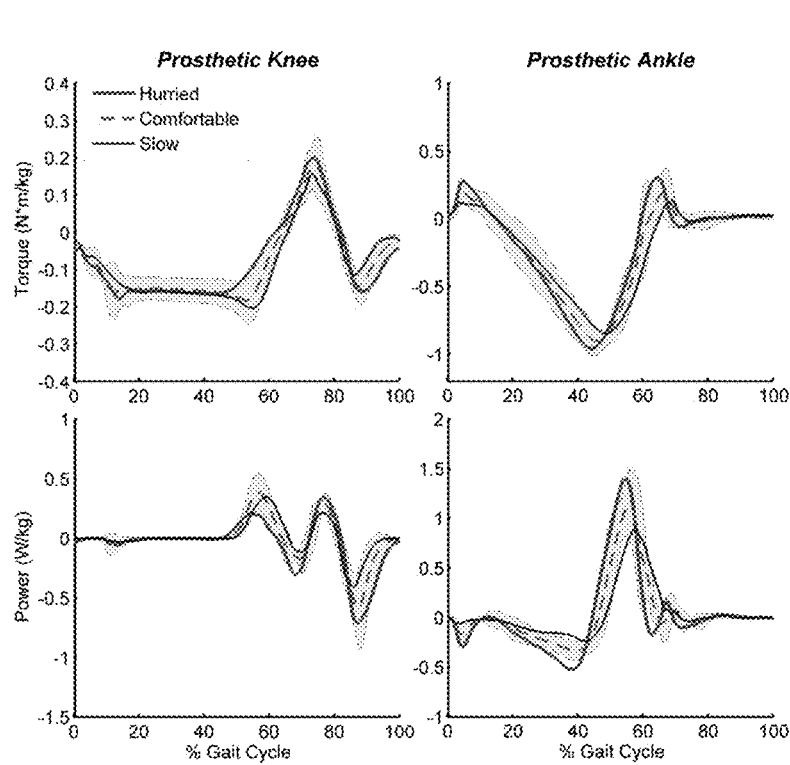
FIG. 9 displays a graph of group-averaged knee and ankle torques and powers of multiple transfemoral amputees using prosthesis 10 and control board 150 to walk up a ramp (incline) at various speeds.
Figure 10:
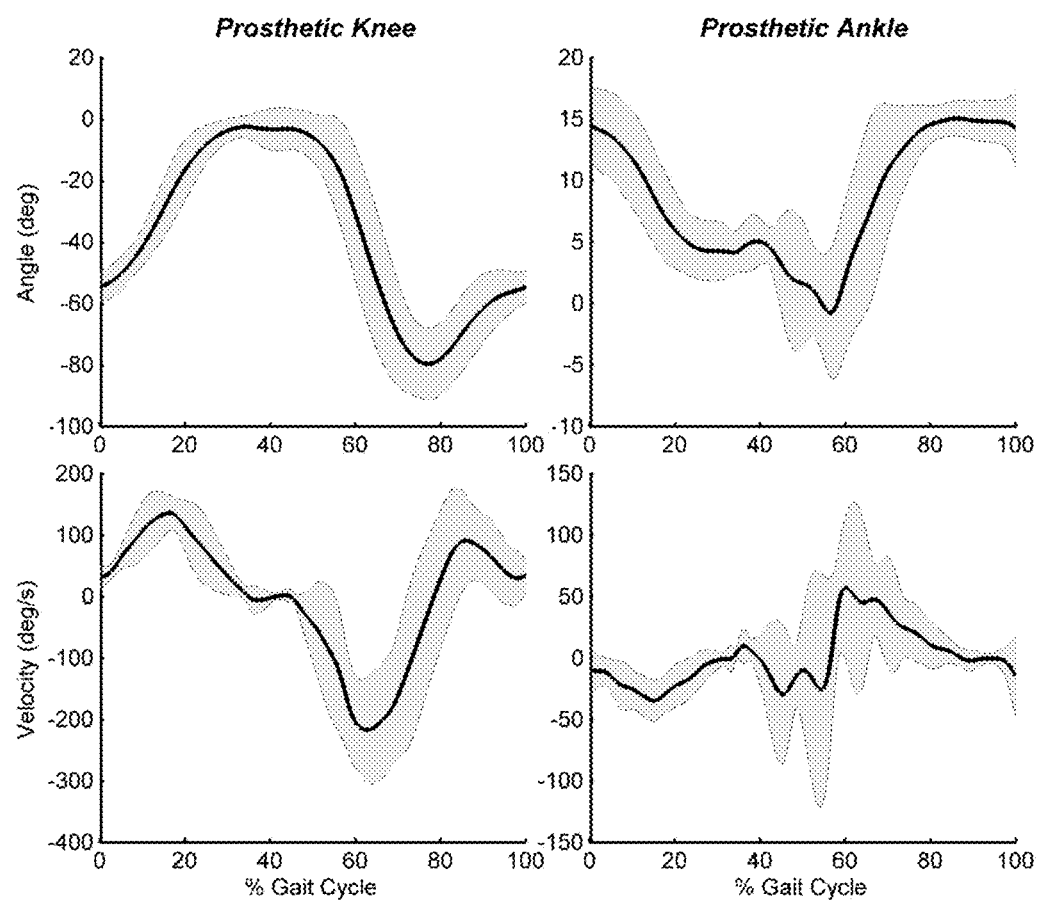
FIG. 10 displays a graph of group-averaged knee and ankle angles and velocities of multiple transfemoral amputees using prosthesis 10 and control board 150 to ascend stairs.

FIGS. 6-10 display results of using prosthesis 10. Power data in FIGS. 6-10 are normalized by user mass (kg) and one standard deviation of the comfortable speed condition is shown. FIG. 6 displays joint angles and velocities plotted across a gait cycle (where 0% of the gait cycle reflects the start of stance 1 and 100% of the gait cycle reflects the end of swing 2). As speed increases, peak ankle dorsiflexion and plantar flexion increase. FIG. 7 displays joint power plotted across a gait cycle. FIGS. 8-10 display joint angle and power plotted against a gait cycle during walking (FIG. 8), ramp ascent/descent (FIG. 9), and stair ascent/descent (FIG. 10). Individual user averages and standard deviations are displayed. Walking and ramp ascent kinematics and kinetics demonstrate controlled plantar flexion, controlled dorsiflexion, and powered plantar flexion. While climbing stairs, users had similar knee kinematics to nonamputee users, a smooth development of knee power in early to mid-stance, and a burst of ankle power in late stance. Ramp descent and stair descent kinematics demonstrate users' ability to use stance phase knee flexion during these modes.

EXPERIMENTAL RESULTS

The system described above was tested on several transfemoral (above-knee) amputee patients. Amputation level varied from knee disarticulation to the proximal third of the femur. All had Medicare functional classification levels 3 or higher. Amputees were fit to a powered knee and ankle prosthesis by a certified prosthetist during these tests. In these fitting sessions, users began by walking between parallel bars to become comfortable using the assistive device. Initial state machine impedance parameters were set to nominal values determined during pilot tests across users. Impedance parameters were altered as necessary to achieve comfortable, safe ambulation. Input from the user, clinicians, and engineers was used to tune the prosthesis for level ground walking, ramp ascent, ramp descent, stair ascent, and stair descent. For all modes, users initially ambulated at their self-selected speed.

Level Ground Walking and Ramp Ascent.

For level ground walking and ramp ascent, the control boards described herein modulated joint impedance as functions of joint angle or axial load. Ankle stiffness was modulated as a function of ankle angle during stance to provide a cushioned heel strike and increased resistance to dorsiflexion as the user progressed through stance. In late stance, knee stiffness, knee equilibrium angle, and ankle equilibrium angle were modulated as a function of decreasing axial load in order to smoothly generate power during the stance to swing transition.

Once users were accommodated to the device, level and incline bocks of walking trials were collected. Within each block, users walked at their self-selected comfortable, hurried, and slow speeds. An average of 20 strides were collected per condition. No additional parameter tuning was performed across speeds. Knee power and ankle power were computed as the product of commanded joint torque and joint velocity.

All users were able to modulate their walking speed on both level and incline walking surfaces, the results of which are shown in Table 3.

TABLE 3

|  | TF1 | TF2 | TF3 | TF4 | TF5 | TF6 | TF7 | Mean | (Std. Dev.) | Change |
|---|---|---|---|---|---|---|---|---|---|---|
| Slow, Level | 0.49 | 0.64 | 0.67 | 0.71 | 0.92 | 0.64 | 0.59 | 0.66 m/s | (0.13) | −24.1% |
| Comfortable, Level | 0.82 | 0.92 | 0.81 | 0.85 | 1.16 | 0.73 | 0.84 | 0.88 m/s | (0.14) | — |
| Hurried, Level | 1.08 | 1.16 | 1.10 | 1.08 | 1.39 | 1.07 | 1.02 | 1.13 m/s | (0.12) | 28.9% |
| Slow, Incline | 0.52 | 0.56 | 0.65 | 0.61 | 0.91 | 0.61 | 0.51 | 0.62 m/s | (0.14) | −23.0% |
| Comfortable, Incline | 0.67 | 0.81 | 0.76 | 0.77 | 1.07 | 0.73 | 0.86 | 0.81 m/s | (0.13) | — |
| Hurried, Incline | 0.85 | 1.08 | 0.91 | 0.95 | 1.32 | 0.84 | 1.12 | 1.01 m/s | (0.17) | 24.9% |

Decreases and increases from their comfortable speeds were between 23 and 29% on average across users. All pairwise increases or decreases in walking speed were statistically significant. As shown in FIGS. 6 and 8, as speed increased, increases of peak ankle dorsiflexion and plantar flexion were observed as measured by ankle position sensor 54. As shown in FIGS. 7 and 9, for increasing speed, negative and positive ankle power increased during stance. These trends and magnitudes are comparable to non-amputees at similar speeds, especially from mid to late stance. The data suggest that the ankle of prosthesis provides body support throughout stance and forward propulsion in late stance, and increases power as speed increases, similar to the plantar flexors of a sound limb.

Users appropriately timed and smoothly performed the transition from stance to swing, since the transition was facilitated through altering stance 2 impedance parameters as a function of a decreasing axial load. As shown in FIGS. 6 and 8, as speed increased, knee flexion angles were initiated earlier during both level and incline walking. In addition, knee flexion velocities on the incline and ankle plantarflexion velocities on both surfaces increased with speed. Collectively, these results suggest the device was keeping up with each user as they increased speed. In our experience, the stance to swing transition can be a "sticking" point in terms of amputees feeling non-smooth behaviors of the device. In addition, a poorly-timed stance to swing transition can negatively affect a user's perception of whether or not the device will be ready for a subsequent heel strike. Thus, one intention of these strategies was to smooth the prosthesis response between late stance and swing flexion states (the results of which are displayed in the graph at FIG. 5B), while another was to initiate swing sufficiently early such that each user was confident the device would be prepared for a subsequent heel strike. Anecdotally, the feedback received from these users regarding this transition was consistently positive.

In addition to the trends of smoother power generation and powered ankle pushoff more similar to non-amputee gait, these control algorithms resulted in a reduced configuration time. The results presented for both level and incline walking required no adjustments in tuning parameters across speed and only one consistent change was made from level to incline conditions (i.e., a 10 degree decrease in final knee flexion equilibrium angle during stance 2).

Furthermore, despite various etiologies, genders, amputation levels, heights and weights, proportionality constants C governing decreasing knee stiffness, swing initiation and powered plantar flexion did not vary (1.0, 1.0 and 1.5, respectively) across users. In addition, final plantar flexion equilibrium angles were 10-12°. Final knee flexion equilibrium angles were an exception as they had larger variations (45-70°). These differences were needed to achieve ground clearance for the various amputation levels while the distance between the knee and ankle was fixed. In embodiments of the lower limb assistive device that do not include this limitation, these differences obviously would not be required.

Ramp Descent.

Figure 11:
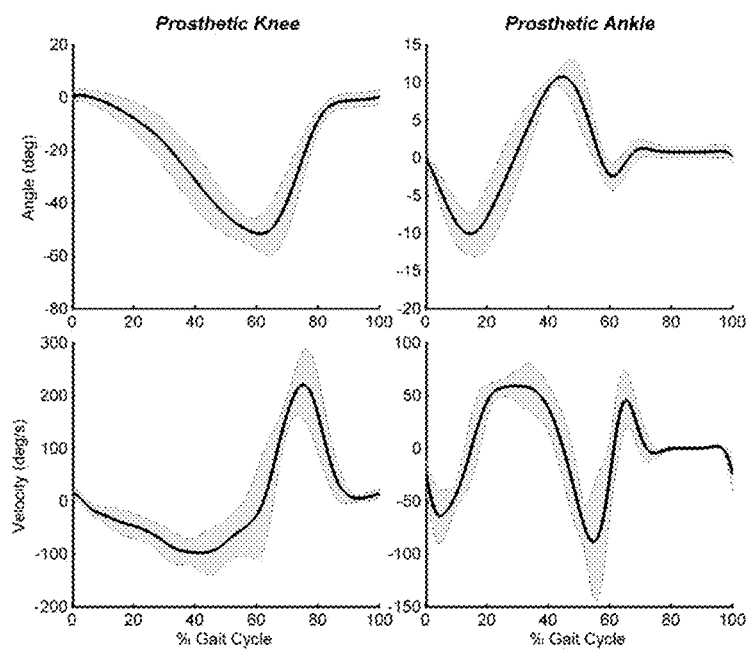
FIG. 11 displays a graph of group-averaged knee and ankle angles and velocities of multiple transfemoral amputees using prosthesis 10 and control board 150 to descend a ramp. One standard deviation of the data across subjects is shown.
Figure 12:
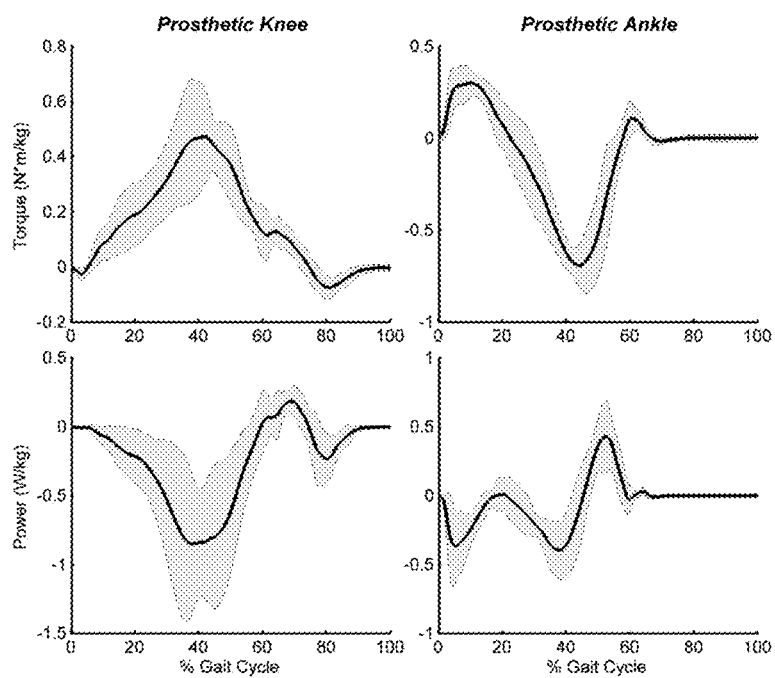
FIG. 12 displays a graph of group-averaged knee and ankle torques and powers of multiple transfemoral amputees using prosthesis 10 and control board 150 to descend a ramp. One standard deviation of the data across subjects is shown.

The early stance (stance 1 state) of ramp descent is primarily controlled to absorb power at the knee and ankle joints of a prosthesis, as shown in FIGS. 11 and 12. However, the control of the late stance to swing transition is important, as a poorly timed stance to swing transition can result in the user dragging the toe of prosthesis as she descends the stairs, which can impair balance. To address these challenges, for ramp descent in late stance (stance 2), knee stiffness, knee equilibrium angle, and ankle equilibrium angle were modulated as a function of decreasing axial load in order to smoothly generate power during and appropriately time the stance to swing transition. With training from a clinician, users were able to walk down the incline using a reciprocal gait without dragging the toe of the prosthesis, indicated by smooth knee angle and velocity profiles of these users as shown in FIG. 11.

Stair Ascent and Descent.

Figure 13:
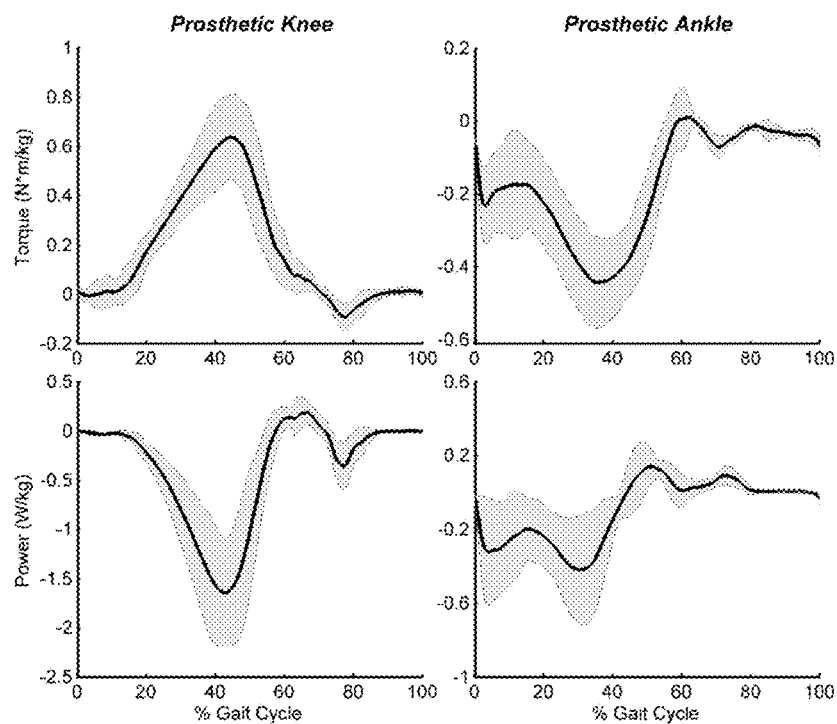
FIG. 13 displays a graph of group-averaged knee and ankle torques and powers of multiple transfemoral amputees using prosthesis 10 and control board 150 to descend stairs. One standard deviation of the data across subjects is shown.
Figure 14:
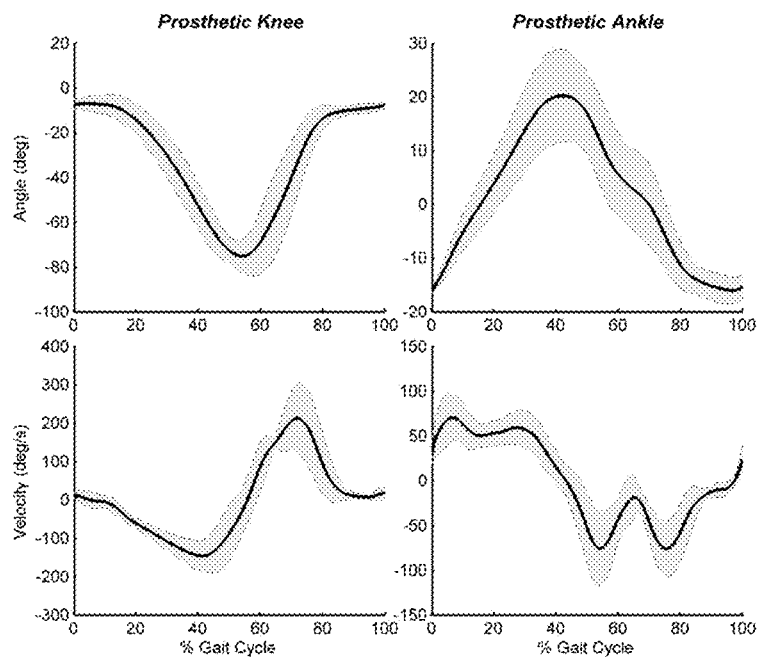
FIG. 14 displays a graph of group-averaged knee and ankle angles and velocities of multiple transfemoral amputees using prosthesis 10 and control board 150 to descend stairs. One standard deviation of the data across subjects is shown.

For stair ascent during stance 1 and stance 2, knee equilibrium angle and in stance 2 ankle equilibrium angle were modulated as a function of increasing axial load such that knee and ankle power was generated as load on the prosthesis increased. For stair descent during stance 1, ankle equilibrium angle was modulated as a function of increasing axial load such that power was dissipated at the ankle (shown in the graph at FIG. 13) as it moves from a plantarflexed angle to a dorsiflexed angle (shown in the graph at FIG. 14).

Figure 15:
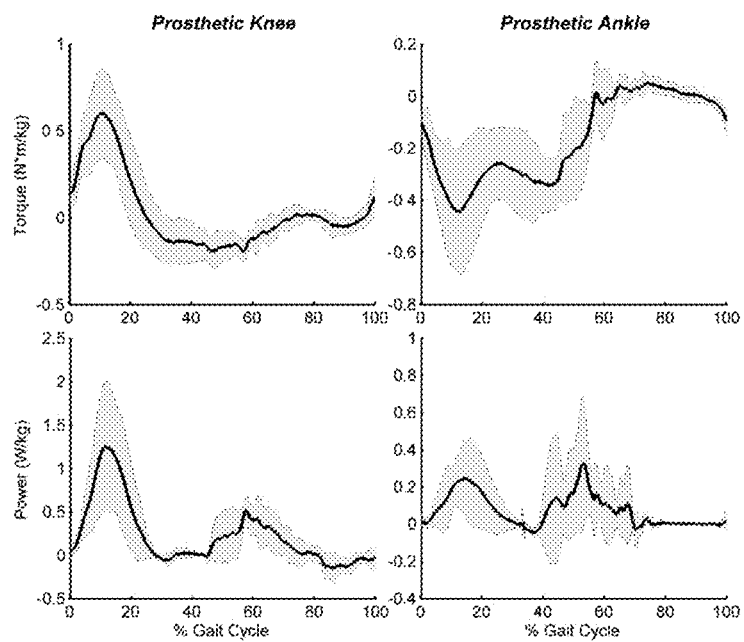
FIG. 15 displays a graph of group-averaged knee and ankle torques and powers of multiple transfemoral amputees using prosthesis 10 and control board 150 to ascend stairs. One standard deviation of the data across subjects is shown.

All users were coached by a clinician on how to perform stair ascent and stair descent with a reciprocal gait (i.e., placing one foot in front of the other). As in the case of operation in other modes and states, impedance parameters that were not otherwise adjusted as described herein were adjusted in a manner already known in the art. For instance, during users' initial attempts at stair ascent, knee stiffness during stance 1 and stance 2 was reduced (e.g., to a value of 2) such that they could practice ascending with a reciprocal gait. None of the users tested had performed this task in this manner post-amputation. When users were comfortable with the task, knee stiffness was increased to the point where a user could use the prosthesis to assist herself up the stairs (e.g., values ranging from 3 to 4.5) rather than pulling herself up with the handrails or using excessive vaulting strategies in her intact limb. While climbing stairs, users had a smooth development of knee power in early to mid-stance and a burst of ankle power in late stance, as shown in the graphs at FIGS. 10 and 15. Prosthesis knee and ankle power was not generated until the user was ready for it; the timing of this stance state power generation was dependent on when the user shifted her weight onto the prosthesis.

Sit-to-Stand.

Figure 16:
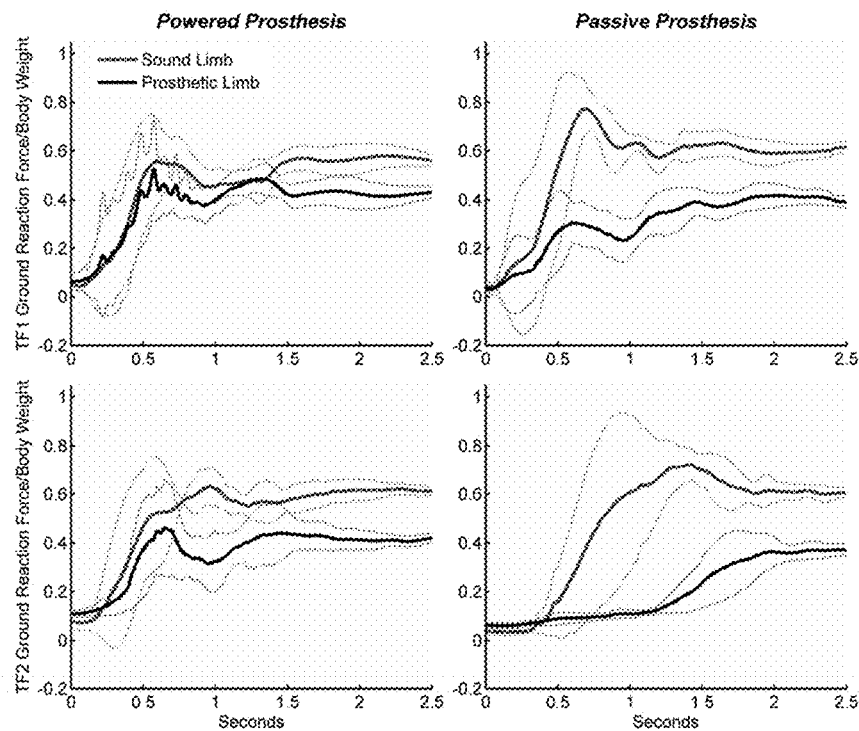
FIG. 16 displays a graph of ground reaction force data (from the prosthetic limb and sound limb) of two subjects (TF1, top row, and TF2, bottom row) using powered prosthesis 10 and control board 150 to perform the sit-to-stand task (left column) in comparison to their passive prescribed prostheses (right column). In both subjects, limb loading symmetry is improved using powered prosthesis 10 and control board 150.

For sit-to-stand, knee and ankle equilibrium angles were adjusted as a function of increasing axial load, such that knee and ankle power was generated as load on the prosthesis increased. Similar to stair ascent, knee and ankle stiffness initially started off low while users became comfortable with the sit-to-stand task. Knee and ankle stiffness was increased to the point where users did not have to rely on handrails to perform the task. Ground reaction forces shown at FIG. 16 were measured by separate force plates located under each foot, and demonstrate that users distributed their weight more equally between their lower limbs than while using passive prostheses.

We claim:

1. A system comprising a controller for a powered lower limb assistive device, the system comprising a motorized joint of the assistive device, the controller comprising a microprocessor and being configured to:
   a. receive one or more user-generated signals while the assistive device is operating in a mode and a state, wherein the mode represents a particular type of activity of the assistive device and the state represents a particular period of operation of the assistive device during a mode;
   b. determine an amount of load on the assistive device using information in the one or more user-generated signals;
   c. select one or more joint impedance parameters of the assistive device for adjustment, selected from the group consisting of a stiffness parameter, a damping parameter, and an equilibrium angle parameter, wherein the one or more selected joint impedance parameters are selected depending upon the mode and the state in which the device is operating; and
   d. within the mode and state in which the device is operating, continuously adjusting the one or more selected joint impedance parameters as a function of the amount of load on the assistive device, and
   e. initiate a signal that controls the motorized joint using the one or more adjusted joint impedance parameters.

2. The system of claim 1, where the controller is configured to adjust the selected joint impedance parameters as a function of the amount of load on the assistive device for at least the modes of ramp ascent and ramp descent.

3. The system of claim 1, where the mode of the assistive device is sit-to-stand.

4. The system of claim 1, further comprising the assistive device.

5. The system of claim 1, where the controller is for a powered lower limb assistive device having a knee joint and an ankle joint.

6. The system of claim 1, where the load is an axial load.

7. The system of claim 1, where the load is a torque or a moment.

8. The system of claim 1, the controller being further configured to:
   a. receive one or more user-generated signals containing information about the ankle angle of the assistive device; and
   b. adjust the stiffness of the ankle joint of the assistive device as a function of the ankle angle when the assistive device is in an ambulation mode.

9. The system of claim 8, further comprising the assistive device.

10. The system of claim 1, wherein the selected joint impedance parameters comprise a stiffness parameter.

11. The system of claim 1, wherein the selected joint impedance parameters comprise a damping parameter.

12. The system of claim 1, wherein the selected joint impedance parameters comprise a knee stiffness parameter when the assistive device is in a walking mode and a stance state, a ramp ascent mode and a stance state, and a ramp descent mode and a stance state.

13. The system of claim 1, wherein the selected joint impedance parameters comprise an ankle equilibrium angle parameter when the assistive device is in a walking mode and a stance state, a ramp ascent mode and a stance state, and a ramp descent mode and a stance state.

14. The system of claim 1, wherein the selected joint impedance parameters comprise a knee equilibrium angle parameter when the assistive device is in a walking mode and a stance state, a ramp descent mode and a stance state, and a ramp descent mode and a stance state.

15. The system of claim 1, wherein the selected joint impedance parameters comprise knee stiffness, ankle equilibrium angle, and knee equilibrium angle parameters when the assistive device is in a walking mode and a stance state, a ramp ascent mode and a stance state, and a ramp descent mode and a stance state.

16. The system of claim 1, wherein the selected joint impedance parameters comprise a knee stiffness parameter when the assistive device is in a ramp ascent mode and a stance state and in a ramp descent mode and a stance state.

17. The system of claim 1, wherein the selected joint impedance parameters comprise an ankle equilibrium angle parameter when the assistive device is in a ramp ascent mode and a stance state and in a ramp descent mode and a stance state.

18. The system of claim 1, wherein the selected joint impedance parameters comprise a knee equilibrium angle parameter when the assistive device is in a ramp ascent mode and a stance state and in a ramp descent mode and a stance state.

19. The system of claim 1, wherein the selected joint impedance parameters comprise knee stiffness, ankle equilibrium angle, and knee equilibrium angle parameters when the assistive device is in a ramp ascent mode and a stance state and in a ramp descent mode and a stance state.

20. The system of claim 1, wherein when the assistive device is in a stair ascent mode and in a stance state, the selected joint impedance parameters comprise an ankle equilibrium angle parameter.

21. The system of claim 1, wherein when the assistive device is in a stair descent mode and in a stance state, the selected joint impedance parameters comprise an ankle equilibrium angle parameter.

22. The system of claim 1, wherein when the assistive device is in a sit-to-stand mode and a sit-to-stand state, the selected joint impedance parameters comprise knee equilibrium angle and ankle equilibrium angle parameters.

* * * * *